United States Patent
Ito

(10) Patent No.: US 10,156,502 B2
(45) Date of Patent: Dec. 18, 2018

(54) TISSUE PIECE TREATING METHOD IN WHICH LIQUID CHEMICAL IS STIRRED BY SUPPLYING AND DRAINING LIQUID CHEMICAL

(71) Applicants: Sakura Seiki Co., Ltd., Chikuma-shi, Nagano (JP); Sakura Finetek Japan Co., Ltd., Chuo-ku, Tokyo (JP)

(72) Inventor: Atsuo Ito, Chikuma (JP)

(73) Assignees: SAKURA SEIKI CO., LTD., Nagano (JP); SAKURA FINETEK JAPAN CO., LTD., Tokyo (JP)

( * ) Notice: Subject to any disclaimer, the term of this patent is extended or adjusted under 35 U.S.C. 154(b) by 0 days.

(21) Appl. No.: 14/900,476

(22) PCT Filed: Jul. 1, 2014

(86) PCT No.: PCT/JP2014/067502
§ 371 (c)(1),
(2) Date: Dec. 21, 2015

(87) PCT Pub. No.: WO2015/002179
PCT Pub. Date: Jan. 8, 2015

(65) Prior Publication Data
US 2016/0153875 A1    Jun. 2, 2016

(30) Foreign Application Priority Data
Jul. 5, 2013  (JP) ................. 2013-142054

(51) Int. Cl.
G01N 1/28     (2006.01)
G01N 1/31     (2006.01)

(52) U.S. Cl.
CPC ......... *G01N 1/31* (2013.01); *G01N 2001/315* (2013.01)

(58) Field of Classification Search
None
See application file for complete search history.

(56) References Cited

U.S. PATENT DOCUMENTS

| 7,371,346 B2 * | 5/2008 | Windeyer | G01N 1/31 422/536 |
| 8,481,283 B2 * | 7/2013 | O'Leary | A01N 1/0231 435/40.5 |
| 9,488,553 B2 * | 11/2016 | Ito | G01N 1/31 |
| 2005/0186114 A1 * | 8/2005 | Reinhardt | B01L 9/52 422/65 |

FOREIGN PATENT DOCUMENTS

| EP | 2278295 A1 * | 1/2011 |
| JP | 5719371 | 4/1982 |
| JP | 57019371 B2 * | 4/1982 |
| JP | 2798430 | 9/1998 |
| JP | 10253512 | 9/1998 |
| JP | 4072298 * | 5/2001 |
| JP | 4072298 | 4/2008 |
| JP | 4072298 B2 * | 4/2008 |
| JP | 2009293983 | 12/2009 |
| JP | 2010160153 | 7/2010 |
| JP | 201218167 | 1/2012 |

OTHER PUBLICATIONS

Sakura Seiki Co., Ltd., et al., International search report for PCT/JP2014/067502, (dated Oct. 7, 2014).

* cited by examiner

*Primary Examiner* — Ralph J Gitomer
(74) *Attorney, Agent, or Firm* — William Thomas Babbitt; Leech Tishman Fuscaldo & Lampl, Inc.

(57) ABSTRACT

The present invention addresses a problem of providing a tissue piece treating method and a tissue piece treating apparatus by which treatment of a tissue piece by each of liquid chemicals can be favorably performed and a running cost can be reduced. In order to address the problem, in a tissue piece treating method in a tissue piece treating apparatus (30) for executing an immersion treatment process by each of the liquid chemicals by supplying the liquid chemicals with different types into a treatment tank (40) in which a basket (42) accommodating the tissue piece is disposed in a predetermined order, a liquid supply/drain cycle in which the liquid chemical in such an amount that the entire basket (42) is exposed in the treatment tank (40) is drained from the treatment tank (40) during the execution of the immersion treatment process by each of the liquid chemicals, and the drained liquid chemical is supplied into the treatment tank (40) so that the entire basket (42) is immersed is repeatedly performed so as to agitate the liquid chemical.

7 Claims, 11 Drawing Sheets

FIG.1

| PROCESS | PURPOSE | LIQUID CHEMICAL NAME | CONCENTRATION | TREATMENT TIME | AGITATION |
|---|---|---|---|---|---|
| 1 | DEHYDRATION | ALCOHOL | D 1 | T 1 | REQUIRED |
| 2 | DEHYDRATION | ALCOHOL | D 2 | T 2 | REQUIRED |
| 3 | DEHYDRATION | ALCOHOL | D 3 | T 3 | REQUIRED |
| 4 | DEHYDRATION | ALCOHOL | D 4 | T 4 | REQUIRED |
| 5 | DEHYDRATION | ALCOHOL | D 5 | T 5 | REQUIRED |
| 6 | DEGREASING | XYLENE | D 6 | T 6 | REQUIRED |
| 7 | DEGREASING | XYLENE | D 7 | T 7 | REQUIRED |
| 8 | DEGREASING | XYLENE | D 8 | T 8 | REQUIRED |
| 9 | PENETRATION | PARAFFIN | D 9 | T 9 | NOT REQUIRED |
| 10 | PENETRATION | PARAFFIN | D 10 | T 10 | NOT REQUIRED |
| 11 | PENETRATION | PARAFFIN | D 11 | T 11 | NOT REQUIRED |

TISSUE PIECE TREATING METHOD IN WHICH LIQUID CHEMICAL IS STIRRED BY SUPPLYING AND DRAINING LIQUID CHEMICAL

CROSS-REFERENCE TO RELATED APPLICATION

This is a 371 application claiming the benefit of International Patent Application No. PCT/JP2014/067502, filed Jul. 1, 2014, which claims priority to Japanese Patent Application No. 2013-142054, filed Jul. 5, 2013.

TECHNICAL FIELD

The present invention relates to a tissue piece treating method and a tissue piece treating apparatus for applying immersion treatment to a tissue piece by supplying/draining different kinds of liquid chemical having different concentrations in a predetermined order in a treatment tank accommodating the tissue piece.

BACKGROUND ART

In hospitals and labs, in order to create microscope specimens and the like from a tissue piece sampled from a living thing, a tissue piece treating apparatus for automatically performing each of treatments of fixing, dehydrating, degreasing, substitution of the tissue piece is used.

In a main body of the tissue piece treating apparatus, a treatment tank for performing each of the aforementioned treatments is provided. Moreover, a basket for accommodating the tissue piece is arranged inside the treatment tank.

In the tissue piece treating apparatus, a plurality of liquid chemical tanks storing each of the liquid chemicals used for treatment of the tissue piece in the basket and having different liquid chemical concentrations in order is provided. Moreover, a paraffin tank used for paraffin embedding is provided separately from the liquid chemical tanks.

Each of the liquid chemical tanks and the paraffin tank is connected to a rotary valve as a selection valve provided in the main body, and the rotary valve is connected to the treatment tank through an opening/closing valve.

Thus, each of the liquid chemical tanks and the paraffin tank can be connected to the treatment tank by being selected by the rotary valve.

Furthermore, the treatment tank can be brought into a pressurized or depressurized state by a pump, and when the treatment tank is brought into the depressurized state, the liquid chemical or paraffin can be supplied into the treatment tank from any one of the liquid chemical tanks and the paraffin tank selected by the rotary valve.

Moreover, the liquid chemical or paraffin brought into contact with the tissue piece having been supplied to the treatment tank and inserted into the basket is returned to the original tank by bringing the inside of the treatment tank into the pressurized state by the pump.

Since the rotary valve, the opening/closing valve, and the pump are controlled by a control unit, the tissue specimen can be sequentially subjected to immersion treatment with predetermined liquid chemicals and with the paraffin in accordance with a treatment order of the tissue specimen set in advance by the control unit.

In this tissue piece treating apparatus, in order to promote penetration of the liquid chemical to the tissue piece and substitution with a liquid contained in the tissue, concentration of the liquid chemical close to an interface between the tissue piece and the liquid chemical needs to be kept high.

Moreover, in the case of a tissue piece which is soft and has many gaps and tissue complicated in itself, if air bubbles enter a depth of the gap formed by the complicated tissue, the air bubbles cannot be removed easily, and the liquid chemical having entered into such gaps in a preceding process can remain without being drained in some cases.

Thus, the liquid chemical supplied into the treatment tank is agitated during the immersion treatment in order to keep the concentration of the liquid chemical close to the interface between the tissue piece and the liquid chemical high and to remove the air bubbles in the gaps of the tissue piece and liquid chemical in the preceding process.

Regarding the agitation of the liquid chemical in the treatment tank in the prior-art tissue piece treating apparatus, provision of a stirrer in order to agitate the liquid chemical by rotation of the stirrer or rotation of a sample basket itself accommodating the tissue piece have been examined, for example.

However, in the case of agitation using the stirrer, since the stirrer is driven by a magnet disposed outside the treatment tank through a wall surface of a bottom portion of the treatment tank, the driving force is poor, and since the stirrer can be provided only at a portion such as a bottom portion, a side wall or the like of the treatment tank, a sufficient amount of the liquid chemical cannot be agitated and moreover, since agitation can hardly affect a spot close to a center part of the treatment tank, sufficient agitation is not performed.

Moreover, in the case of rotation and agitation of the sample basket itself, since a rotary shaft is provided by protruding outward from a shaft hole provided in the bottom portion of the treatment tank, a seal structure of the shaft hole portion or the like is needed, which makes the structure complicated. Moreover, since an ordinary sample basket accommodates many tissue pieces, in a spot close to a center of the sample basket, even if the sample basket itself is rotated, the agitated liquid chemical cannot enter the spot close to the center part easily.

Thus, a tissue piece treating apparatus is proposed in which a pump and a valve are operated and a liquid supply/drain cycle is repeatedly performed in which a predetermined amount of liquid chemical is drained to a corresponding liquid chemical tank to such a degree that the tissue piece accommodated in the treatment tank is not exposed from the liquid chemical during a tissue piece treatment process in which the tissue piece is subjected to an immersion treatment in a liquid chemical in the treatment tank for a predetermined time, and after the predetermined amount of the liquid chemical is drained, the same amount of the liquid chemical is supplied into the treatment tank again from the liquid chemical tank so that the liquid chemical is agitated only by repeating liquid supply/drain of the predetermined amount of the liquid chemical supplied into the treatment tank (see PTL 1).

According to this tissue piece treating apparatus, agitation of the entire liquid chemical in the treatment tank can be reliably performed, and the agitation is possible with a simple structure without providing driving means such as a motor for agitation of the liquid chemical.

CITATION LIST

Patent Literature

PTL 1: Japanese Patent Laid-Open No. 2001-133371

SUMMARY OF INVENTION

Technical Problem

In the aforementioned PTL 1, by repeating supply/drain of the liquid chemical in the treatment tank, the liquid chemical in the treatment tank is agitated.

However, conventionally, supply/drain of the liquid chemical is performed while the tissue piece is immersed in the liquid chemical at all times so that the tissue piece in the treatment tank is not exposed to outside of the liquid chemical. This is based on an idea that the tissue piece in treatment is not brought into contact with air as much as possible.

As illustrated in PTL 1, if the liquid chemical is supplied/drained and the liquid chemical is agitated while the tissue piece is immersed in the liquid chemical, there is a problem that the liquid chemical close to the tissue piece does not move much, and there is a possibility that treatment of the tissue piece by each liquid chemical cannot be performed favorably.

In the case of agitation of the liquid chemical by supplying/draining the liquid chemical while the tissue piece is immersed in the liquid chemical as in PTL 1, a time interval of supply/drain needs to be short (15 minutes interval, for example) in order to promote sufficient agitation.

However, if the time interval of supply/drain is short, driving time of the pump and the like becomes long, and an increase of a running cost such as an increase of electricity usage fees and the like involved with driving of the pump becomes a problem.

Thus, the present invention was made in order to solve the aforementioned problems and has an object to provide a tissue piece treating method and a tissue piece treating apparatus which can favorably treat a tissue piece by each of the liquid chemicals and can reduce a running cost.

Solution to Problem

According to such tissue piece treating method according to the present invention, this is a tissue piece treating method in a tissue piece treating apparatus for executing an immersion treatment process by each of liquid chemicals by supplying each of different types of liquid chemicals in a predetermined order to a treatment tank in which a basket accommodating a tissue piece is disposed inside, characterized in that a liquid supply/drain cycle for draining a liquid chemical in such an amount that the entire basket is exposed in the treatment tank from the treatment tank during execution of the immersion treatment process by each of the liquid chemicals and for supplying the drained liquid chemical into the treatment tank so that the entire basket is immersed is repeatedly executed so as to perform agitation of the liquid chemical.

According to this method, the liquid chemical close to the tissue piece is reliably moved, and treatment of the tissue piece by each of the liquid chemicals can be favorably executed.

Moreover, it may be characterized in that, when the liquid chemical in such an amount that the entire basket is exposed in the treatment tank is drained from the treatment tank, the liquid is drained so that air in the treatment tank is not discharged.

That is, if the liquid chemical in the treatment tank is fully drained, air in the treatment tank can enter the liquid chemical tank. If the air in the treatment tank enters the liquid chemical tank, there is a concern that a pressure in the liquid chemical tank increases and the liquid chemical tank is swollen and deformed. Moreover, the liquid chemical can be easily evaporated in the liquid chemical tank, and an evaporated gas discharged from the liquid chemical tank increases and quickens exhaustion of an air discharge filter provided in a discharge pipe for discharging the evaporated gas. Therefore, by preventing the air in the treatment tank from being discharged, deformation of the liquid chemical tank can be prevented, and quick exhaustion of the air discharge filter can be avoided.

Moreover, it may be characterized in that, in the treatment tank, a liquid level guarantee sensor for detecting the liquid chemical at a liquid level guarantee position which is a position where the entire tissue piece in the basket is immersed in the liquid chemical is provided, and when the liquid chemical in the amount that the entire basket is exposed in the treatment tank is to be drained from the treatment tank, by constituting such that the liquid drain is finished after predetermined time set in advance has elapsed since the liquid level guarantee sensor detected a liquid level of the liquid chemical, the entire basket in the treatment tank is disposed and the air in the treatment tank is prevented from being discharged.

According to this method, by counting in advance and storing the time during which the entire basket is exposed from the liquid chemical and the liquid chemical is not fully drained but slightly remains after the liquid level guarantee sensor detects the level, the air in the treatment tank can be prevented from being discharged at liquid drain, whereby deformation of the liquid chemical tank can be prevented, and quick exhaustion of the air discharge filter can be prevented.

Moreover, it may be characterized in that, in the treatment tank, a liquid supply stop sensor for detecting the liquid chemical at a liquid supply stop position which is a position above an upper surface position of the basket and where liquid supply is stopped is provided, and when the liquid is supplied into the treatment tank so that the entire basket is immersed, the liquid supply is stopped when the liquid supply stop sensor detects the liquid level of the liquid chemical.

According to this method, the entire basket can be reliably immersed in the liquid chemical in the liquid supply.

Moreover, it may be characterized in that, a pressure sensor for detecting a pressure in the treatment tank is provided in the tissue piece treating apparatus, and when the liquid chemical in such an amount that the entire basket is exposed in the treatment tank is drained from the treatment tank, if the pressure sensor detects a pressure drop in the treatment tank, the predetermined time set in advance is reduced and set again and then, when the liquid chemical in the amount that the entire basket is exposed in the treatment tank is drained from the treatment tank, the liquid level guarantee sensor detects the liquid level of the liquid chemical and the liquid drain is finished after the predetermined time set again has elapsed, whereby the entire basket is exposed in the treatment tank and the air in the treatment tank is not discharged.

According to this method, if the air in the treatment tank is discharged in the predetermined time set initially, discharge of the air can be prevented in liquid drain processing the next time by setting the predetermined time again.

Moreover, it may be characterized in that, sensors each capable of detecting a liquid level are provided at a plurality of positions corresponding to a height of each of the baskets in the treatment tank so that the liquid supply/drain cycle can be repeatedly performed in accordance with a height of each basket even if the baskets with different heights are accommodated or a plurality of the baskets is stacked and accommodated, and when the liquid supply/drain cycle is to be performed to the basket with a low height, the sensor provided at a lowermost position is used as the liquid level guarantee sensor, and the liquid supply/drain cycle is performed by using the sensor disposed above the upper surface position of the basket with the low height as the liquid supply stop sensor, while when the liquid supply/drain cycle is to be performed to the basket with a high height or to the baskets each with the low height stacked in plural stages, not the liquid level guarantee sensor corresponding to the basket with the high height or the basket with the low height, but the sensor provided at the lowermost position detects the liquid level of the liquid chemical and then, the liquid drain is finished after the predetermined time set in advance has elapsed, and the liquid supply/drain cycle is performed by using the sensor disposed above the upper surface position of the basket with the high height or the baskets each with the low height stacked in plural as the liquid supply stop sensor.

According to this method, agitation of the liquid chemical can be performed by repeatedly performing the liquid supply/drain cycle to the baskets with various heights. Moreover, since the air in the treatment tank can be prevented from being discharged at the liquid drain, deformation of the liquid chemical tank can be prevented, and quick exhaustion of the air discharge filter can be prevented.

According to the tissue piece treating apparatus according to the present invention, the tissue piece treating apparatus includes: the basket accommodating the tissue piece; the treatment tank in which the basket is disposed; a plurality of the liquid chemical tanks each storing liquid chemical required for treatment of the tissue piece; a treatment tank pipeline having one end connected to a bottom portion of the treatment tank; a plurality of liquid chemical pipelines each having one end connected to each of the liquid chemical tank; a valve having a treatment tank side port to which the other end of the treatment tank pipeline is connected and a plurality of liquid chemical tank side ports to which the other ends of the plurality of liquid chemical pipelines are connected, capable of selecting and connecting any one of the liquid chemical tanks to the treatment tank, and opening/closing a space between the treatment tank pipeline and each of the liquid chemical tanks; a pump for performing liquid supply of the liquid chemical from the liquid chemical tank selected by the valve into the treatment tank and liquid drain from inside the treatment tank to the liquid chemical tank selected by the valve; and a control unit for controlling a selecting operation of the valve, an opening/closing operation, and an operation of the pump and performing the liquid supply/drain operation between the treatment tank and the liquid chemical tank, in which the control unit repeatedly performs a liquid supply/drain cycle in which the pump and the valve are operated and the liquid chemical is drained from the treatment tank in such an amount that the entire basket is exposed in the treatment tank during execution of an immersion treatment process of subjecting the tissue piece to the immersion treatment for predetermined time in the liquid chemical in the treatment tank and the drained liquid chemical is supplied into the treatment tank so that the entire basket is immersed, whereby the liquid chemical is agitated.

By employing this constitution, the liquid chemical close to the tissue piece can be reliably moved, and treatment of the tissue piece by each of the liquid chemicals can be favorably performed.

Moreover, the control unit may be characterized in that, when the liquid chemical in the amount that the entire basket is exposed in the treatment tank is drained from the treatment tank, the liquid drain is performed so that the air in the treatment tank is not discharged.

According to this constitution, since it can be so constituted that the air in the treatment tank is not discharged, deformation of the liquid chemical tank can be prevented, and quick exhaustion of the air discharge filter can be prevented.

Moreover, it may be characterized in that, in the treatment tank, the liquid level guarantee sensor for detecting the liquid chemical at the liquid level guarantee position which is a position where the entire tissue piece in the basket is immersed in the liquid chemical is provided, and the control unit is constituted such that, when the liquid chemical in the amount that the entire basket is exposed in the treatment tank is drained from the treatment tank, the liquid drain is finished after predetermined time set in advance has elapsed since the liquid level guarantee sensor detects the liquid level of the liquid chemical so that the entire basket is exposed in the treatment tank and the air in the treatment tank is not discharged.

By employing this constitution, by counting in advance and storing in the control unit the time during which the entire basket is exposed from the liquid chemical and the liquid chemical is not fully drained but slightly remains after the liquid level guarantee sensor detects the level, the air in the treatment tank can be prevented from being discharged at liquid drain, whereby deformation of the liquid chemical tank can be prevented, and quick exhaustion of the air discharge filter can be prevented.

Moreover, it may be characterized in that, in the treatment tank, the liquid supply stop sensor for detecting the liquid chemical at the liquid supply stop position which is a position above the upper surface position of the basket and where liquid supply is stopped is provided, and when the liquid is supplied into the treatment tank so that the entire basket is immersed, the control unit stops the liquid supply when the liquid supply stop sensor detects the liquid level of the liquid chemical.

According to this constitution, the entire basket can be reliably immersed in the liquid chemical in the liquid supply.

Moreover, it may be characterized in that, the pressure sensor for detecting a pressure in the treatment tank is provided, and when the liquid chemical in such an amount that the entire basket is exposed in the treatment tank is drained from the treatment tank, if the pressure sensor detects a pressure drop in the treatment tank, the control unit reduces and sets again predetermined time set in advance and then, when the liquid chemical in the amount that the entire basket is exposed in the treatment tank is drained from the treatment tank, the liquid level guarantee sensor detects the liquid level of the liquid chemical and the liquid drain is finished after the predetermined time set again has elapsed, whereby the entire basket is exposed in the treatment tank and the air in the treatment tank is not discharged.

According to this constitution, if the air in the treatment tank is discharged in the predetermined time set at the first, discharge of the air can be prevented in liquid drain processing the next time by setting the predetermined time again.

Moreover, it may be characterized in that, sensors each capable of detecting a liquid level are provided in the treatment tank at a plurality of positions corresponding to a height of each of the baskets so that the liquid supply/drain cycle can be repeatedly performed in accordance with the height of each basket even if the baskets with different heights are accommodated or a plurality of the baskets is stacked and accommodated, and when the liquid supply/drain cycle is to be performed to the basket with a low height, the control unit performs the liquid supply/drain cycle by using the sensor provided at a lowermost position as the liquid level guarantee sensor and the sensor disposed above the upper surface position of the basket with the low height as the liquid supply stop sensor, while when the liquid supply/drain cycle is to be performed to the basket with a high height or to the baskets each with the low height stacked in plural stages, the control unit finishes the liquid drain after predetermined time set in advance has elapsed since the liquid level of the liquid chemical is detected not by the liquid level guarantee sensor corresponding to the basket with the high height or the basket with the low height but by the sensor provided at the lowermost position and then, the control unit performs the liquid supply/drain cycle by using the sensor disposed above the upper surface position of the basket with the high height or the baskets each with the low height stacked in plural as the liquid supply stop sensor.

According to this constitution, agitation of the liquid chemical can be performed by repeatedly performing the liquid supply/drain cycle to the baskets with various heights. Moreover, since the air in the treatment tank can be prevented from being discharged at the liquid drain, deformation of the liquid chemical tank can be prevented, and quick exhaustion of the air discharge filter can be prevented.

Advantageous Effects of Invention

According to the tissue piece treating method and the tissue piece treating apparatus of the present invention, since the liquid chemical close to the tissue piece can be reliably moved, the treatment of the tissue piece by each liquid chemical can be favorably performed.

BRIEF DESCRIPTION OF DRAWINGS

FIG. 1 is a table illustrating each process of a tissue piece treating method according to the present invention.

DESCRIPTION OF EMBODIMENTS

Figure 2:
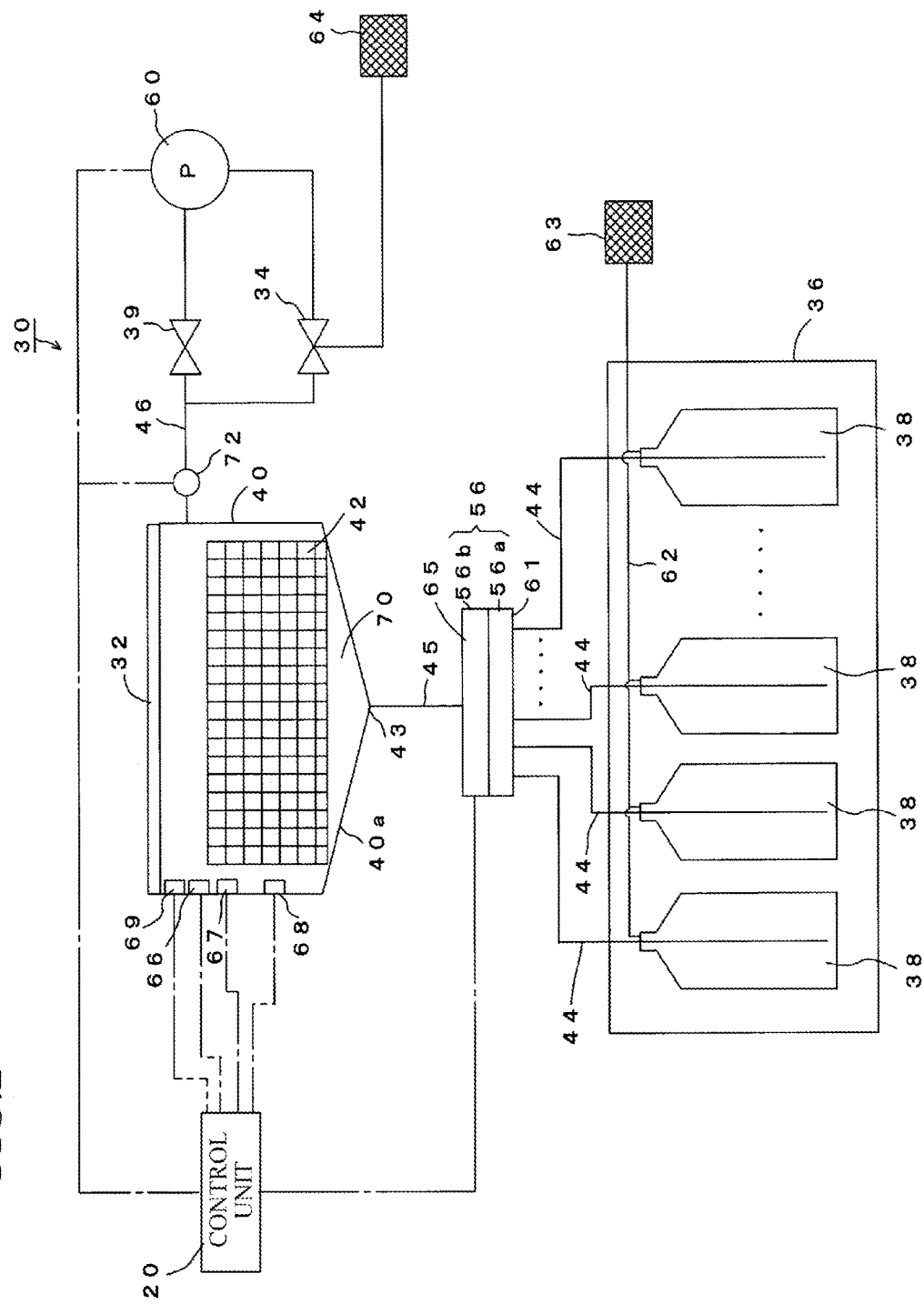
FIG. 2 is an explanatory view illustrating an outline constitution of the tissue piece treating apparatus according to the present invention.

FIG. 1 illustrates an example of a tissue piece treatment process, and FIG. 2 illustrates a constitution of a tissue piece treating apparatus according to this embodiment.

First, the example of the tissue piece treatment process will be described on the basis of FIG. 1.

In order to treat one tissue piece, in order to penetrate paraffin into the tissue piece for embedding fixation in the end, the tissue piece is dehydrated by alcohol and then, the alcohol is substituted with xylene for degreasing. In this embodiment, ethanol is employed for the alcohol, but alcohol is not limited to ethanol.

In dehydration of the tissue piece by alcohol, treatment is performed such that a plurality of types of alcohol with different concentrations is sequentially supplied in the treatment so as to gradually increase the concentration such that, after the alcohol in a preceding process is drained, the alcohol in a subsequent process is supplied.

In substitution of the tissue piece with xylene, too, a plurality of types of xylene with different concentrations is sequentially supplied in the treatment so as to gradually increase the concentration such that, after the xylene in a preceding process is drained, xylene in a subsequent process is supplied similarly to dehydration.

In the tissue piece treating method according to this embodiment, agitation of liquid chemical in the treatment tank is performed by repeating liquid discharge/supply of the liquid chemical from the treatment tank during the tissue piece treatment process after the liquid chemical (alcohol and xylene) is supplied and an immersion treatment of the tissue piece in the liquid chemical is started.

Specifically, during execution of the immersion treatment process by each liquid chemical, the liquid supply/drain cycle in which the liquid chemical in such an amount that the entire basket is exposed in the treatment tank is drained from the treatment tank, and the drained liquid chemical is supplied into the treatment tank so that the entire basket is immersed is repeatedly performed so as to agitate the liquid chemical.

Conventionally, during the immersion treatment process by liquid chemical, it has been considered preferable that the tissue piece is not exposed from the liquid chemical. However, no bad influence is found to be caused by exposure even if the tissue piece is exposed from the liquid chemical as in this embodiment, or rather, since the agitation is performed favorably, dehydration/degreasing effects of the tissue piece are large, and it was found that immersion treatment is sufficiently performed.

Moreover, since the tissue piece is exposed from the liquid chemical once and then, immersed in the liquid chemical again, an effect of washing off a surface of the tissue piece is exerted, and the immersion treatment of the liquid chemical is also considered to be performed effectively.

The tissue piece for which the immersion treatment by alcohol which is a dehydrating agent and xylene which is an intermediate agent is finished is subjected to embedding treatment by paraffin, and the tissue piece is embedded/ fixed. Paraffin supplied into the treatment tank does not have to be agitated in this embodiment.

Constitution of the tissue piece treating apparatus will be described on the basis of FIG. 2.

The tissue piece treating apparatus 30 of this embodiment is a single-tank type device having a single treatment tank 40 for treating the tissue piece provided. The treatment tank 40 has its upper surface open, but the treatment tank 40 is provided capable of being sealed by a sealing lid 32 during treatment by the liquid chemical.

A bottom surface 40a of the treatment tank 40 is inclined so that a center is located at the lowest. At the center of the bottom surface 40a, a supply/drain port 43 is provided. Supply/drain of the liquid chemical into the treatment tank 40 is made through this supply/drain port 43.

In the treatment tank 40, a basket 42 accommodating the tissue piece (not shown) is housed inside. As the basket 42, the one having a cuboid shape is generally employed. Moreover, it is only necessary that a height of the basket 42 is high enough to be reliably accommodated in the treatment tank 40.

Since the basket 42 is a cuboid, its bottom surface is a horizontal surface. On the other hand, since the treatment tank 40 has the bottom surface 40a inclined toward the center, the bottom surface of the basket 42 is not brought into full contact with the bottom surface of the treatment tank 40, but only a peripheral edge portion is in contact with the bottom surface 40a of the treatment tank 40.

Below the treatment tank 40, a plurality of liquid chemical tanks 38 is disposed (FIG. 2 illustrates an empty state).

To each of the liquid chemical tanks 38, one end of a liquid chemical pipeline 44 for feeding the liquid chemical stored in each of the liquid chemical tanks 38 to the treatment tank 40 and through which the liquid chemical drained from the treatment tank 40 flows is connected. The plurality of liquid chemical tanks 38 is accommodated in an accommodating unit 36 provided in the tissue piece treating apparatus 30.

To each of the liquid chemical tanks 38, an air discharge pipe 62 for discharging gas generated in each of the liquid chemical tanks 38 is connected. On an air discharge side end portion of the air discharge pipe 62, an air discharge filter 63 is mounted. As the air discharge filter 63, active coal or the like is used.

The other end of each of the liquid chemical pipelines 44 is connected to a liquid chemical tank side port 61 of a selection valve 56. Here, as the selection valve 56, a rotary valve constituted by a valve seat 56a and a valve plate 56b is used.

On the valve seat 56a, a plurality of liquid chemical tank side ports 61 to which the plurality of liquid chemical pipelines 44 extending from the plurality of liquid chemical tanks 38 is connected is formed. On the other hand, on the valve plate 56b, a treatment tank side port 65 to which one end of a liquid chemical pipeline 45 connected to the treatment tank 40 is connected is formed.

Moreover, the other end of the liquid chemical pipeline 45 is connected to the supply/drain port 43 at the center of the bottom surface of the treatment tank 40.

The selection valve 56 selects one of the plurality of liquid chemical tanks 38 by rotating the valve plate 56b with respect to the valve seat 56a and connects the selected liquid chemical tank 38 to the treatment tank 40. Specifically, the selection valve 56 drives the valve plate 56b by an electric motor or the like, not shown.

In the treatment tank 40, one end of an air pipeline 46 is connected to a side wall surface above a liquid level upper limit position a so as to ensure communication with an air layer above the liquid level upper limit position a of the liquid chemical. The other end of the air pipeline 46 branches to two parts, and to each of the branches, a pressurization-side switching valve 34 and a depressurization-side switching valve 39 are connected. The pressurization-side switching valve 34 and the depressurization-side switching valve 39 are connected to a pressurization side and a depressurization side of the pump 60, respectively. A filter 64 is provided for removing discharged air transported by a pump 60 during depressurization. Supply/drain of the liquid chemical into the treatment tank 40 is performed by operating the pump 60 and by pressurizing/depressurizing the inside of the treatment tank 40.

Moreover, a pressure sensor 72 is provided in a middle portion of the air pipeline. The pressure sensor 72 can measure the pressure in the treatment tank 40 by measuring the pressure inside the air pipeline 46. The pressure sensor 72 is connected to the control unit 20 and measures the pressure inside the treatment tank 40.

The pressure sensor 72 is used for measuring the pressure inside the treatment tank 40 when the liquid supply/drain cycle for supplying/draining the liquid chemical in the treatment tank 40 by pressurization/depressurization of the pump 60 during the tissue piece treatment process is repeated and for counting opening/closing timing of the selection valve 56.

The pressure sensor 72 may be mounted inside the treatment tank 40.

When the liquid chemical is to be supplied into the treatment tank 40, the pressurization-side switching valve 34 is closed, the depressurization-side switching valve 39 is opened, and the pump 60 suctions air in the air pipeline 46. Thus, the internal pressure of the treatment tank 40 becomes negative, and the liquid chemical is pumped up into the treatment tank 40 from the one liquid chemical tank 38 selected by the selection valve 56 through the treatment tank side pipeline 45 and the liquid chemical pipeline 44.

When the liquid chemical in the treatment tank 40 is to be drained, the pressurization-side switching valve 34 is opened, the depressurization-side switching valve 39 is closed, and the pump 60 blows air into the treatment tank 40. Thus, the inside of the treatment tank 40 is pressurized, and the liquid chemical in the treatment tank 40 is returned to the liquid chemical tank 38 side by the selected selection valve 56 through the treatment tank side pipeline 45 and the liquid chemical pipeline 44.

When the liquid chemical in the treatment tank 40 is to be returned to the liquid chemical tank side, the liquid chemical may be returned to the liquid chemical tank 38 side by free-fall by the gravity by making atmospheric air communicate with the inside of the treatment tank 40 without operating the pump 60.

On the side wall surface inside the treatment tank 40, a plurality of sensors capable of detecting the liquid level is provided. Each of the sensors is connected to the control unit 20, respectively, and can cause the control unit 20 to recognize that the liquid level is detected at liquid level detection.

In this embodiment, four sensors are disposed along a vertical direction. In the four sensors, the uppermost sensor is an overflow sensor 69. The overflow sensor 69 is provided close to an upper limit of the treatment tank 40 and detects the liquid level so that the liquid chemical does not overflow from the treatment tank 40.

Below the overflow sensor 69, three sensors are provided. In the three sensors, an uppermost sensor is assumed to be a first liquid level sensor 66, a lowermost sensor to be a second liquid level sensor 68, and a sensor in a middle position to be a third liquid level sensor 67.

These three sensors are provided so that the liquid supply/drain cycle can be reliably executed even if the heights of the baskets accommodated in the treatment tank 40 are different.

In this embodiment, the basket 42 having a size that only one basket can be accommodated in the treatment tank 40 (hereinafter referred to as an ordinary basket in some cases) and a basket 49 (hereinafter referred to as a thin basket in some cases) having approximately a half of the basket 42 in a height direction can be accommodated.

With respect to the ordinary basket 42, the third liquid level sensor 67 at the middle position is provided at a liquid level guarantee position guaranteeing that the tissue piece in the ordinary basket 42 is at a position where the tissue piece is reliably immersed in the liquid chemical. That is, the third liquid level sensor 67 functions as the liquid level guarantee sensor with respect to the ordinary basket 42.

Moreover, with respect to the ordinary basket 42, the first liquid level sensor 66 is provided at a liquid supply stop position located above an upper surface of the ordinary basket 42 and which is a position where the liquid supply is stopped in liquid supply of the liquid chemical. That is, the first liquid level sensor 66 functions as a liquid supply stop sensor with respect to the ordinary basket 42.

On the other hand, with respect to the thin basket 49, the lowermost second liquid level sensor 68 is provided at a liquid level guarantee position guaranteeing that the tissue piece in the thin basket 49 is at a position where the tissue piece is reliably immersed. That is, with respect to the thin basket 49, the second liquid level sensor 68 functions as a liquid level guarantee sensor.

Moreover, with respect to the thin basket 49, the third liquid level sensor 67 is provided at a liquid supply stop position located above an upper surface of the thin basket 49 and which is a position where the liquid supply is stopped in liquid supply of the liquid chemical. That is, the third liquid level sensor 67 functions as a liquid supply stop sensor with respect to the thin basket 49.

The aforementioned first, second, and third liquid level sensors are all connected to the control unit 20. The control unit 20 includes a central processing unit (CPU) and a memory storing a program for causing the central processing unit to perform a predetermined operation.

First Embodiment on Agitation of Liquid Chemical

Figure 3:
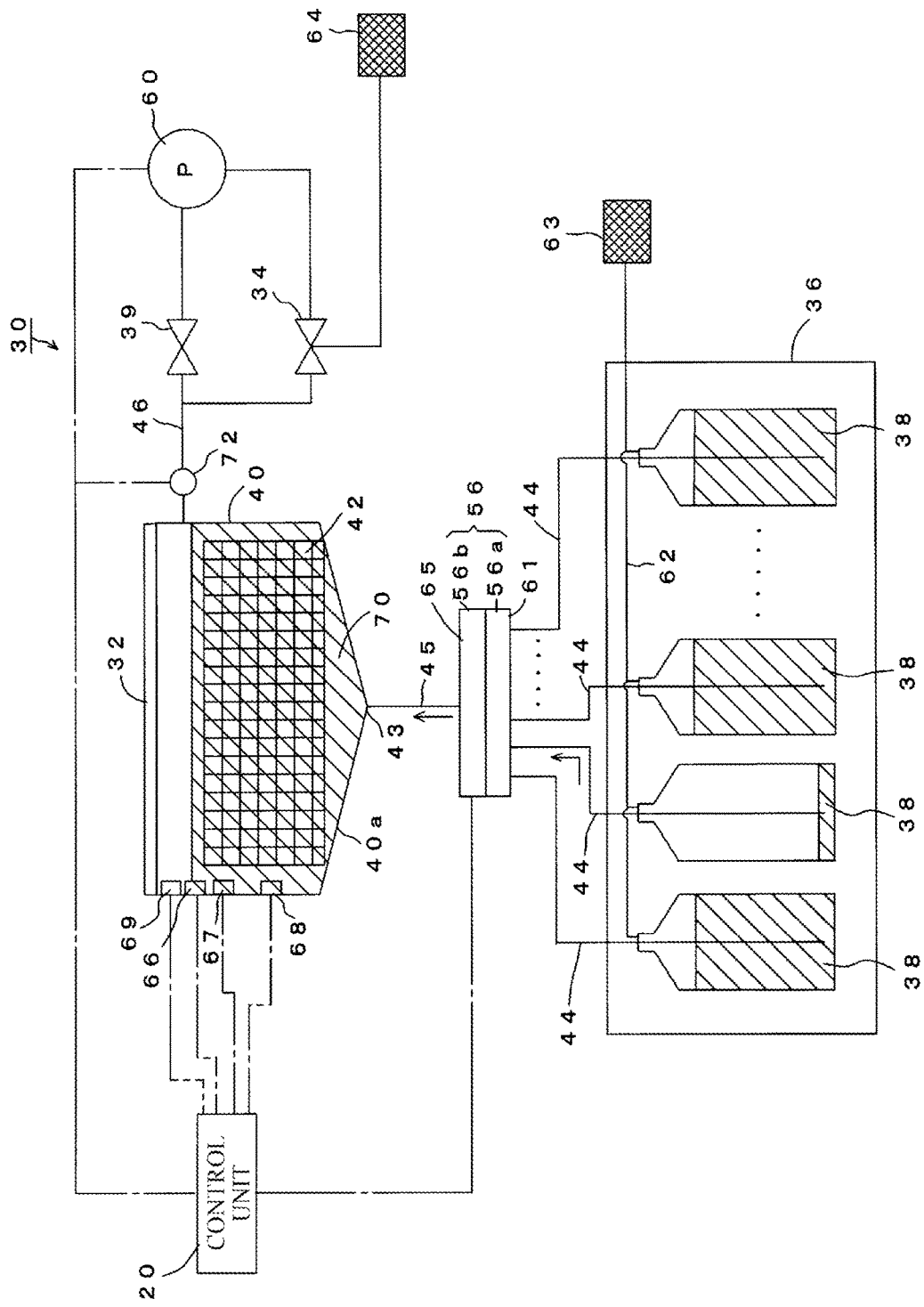
FIG. 3 is an explanatory view illustrating a state in which liquid chemical is supplied into a treatment tank accommodating an ordinary basket.
Figure 4:
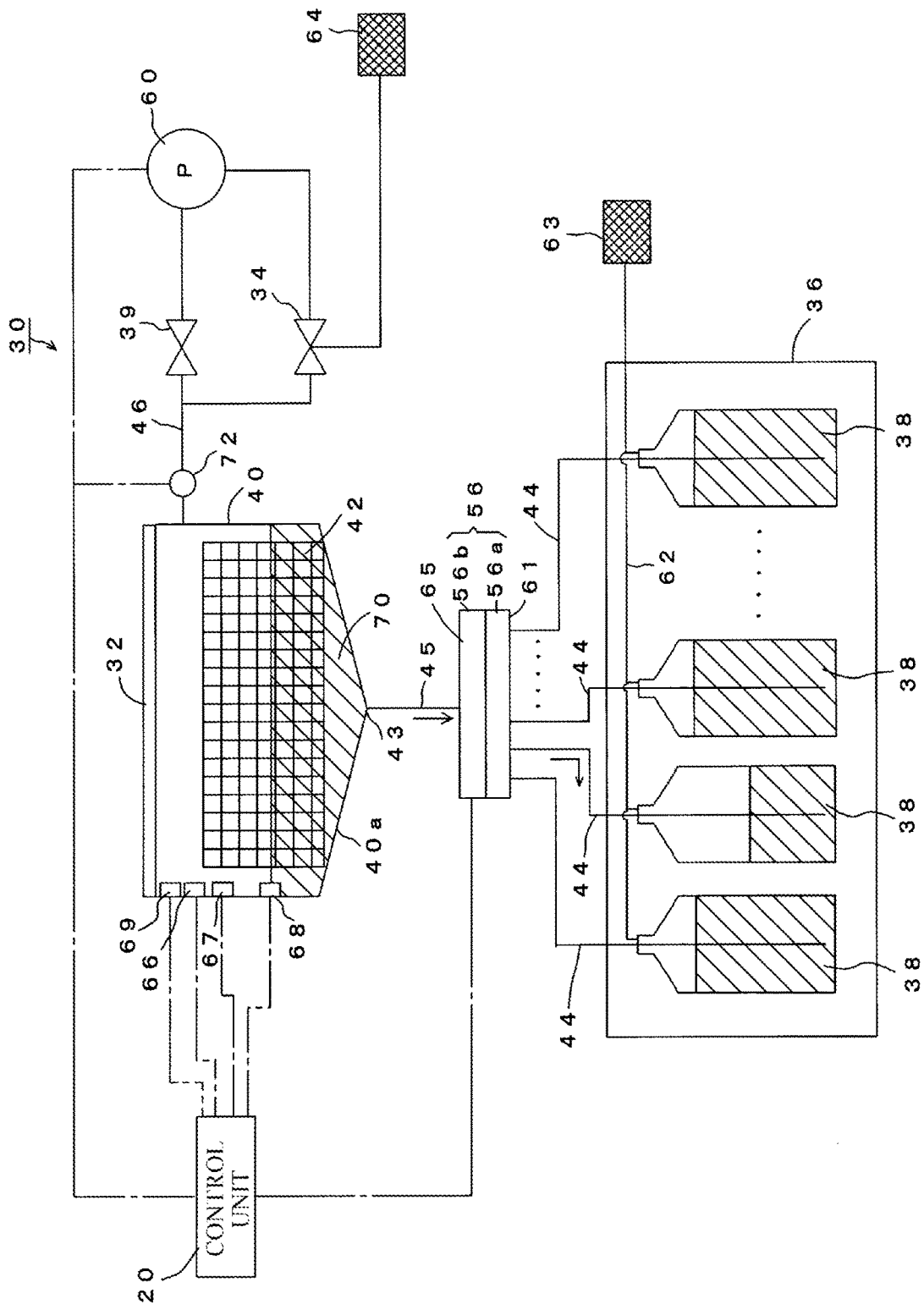
FIG. 4 is an explanatory view illustrating a state in which the liquid chemical is drained to a bottom surface of the basket from the state in FIG. 3.
Figure 5:
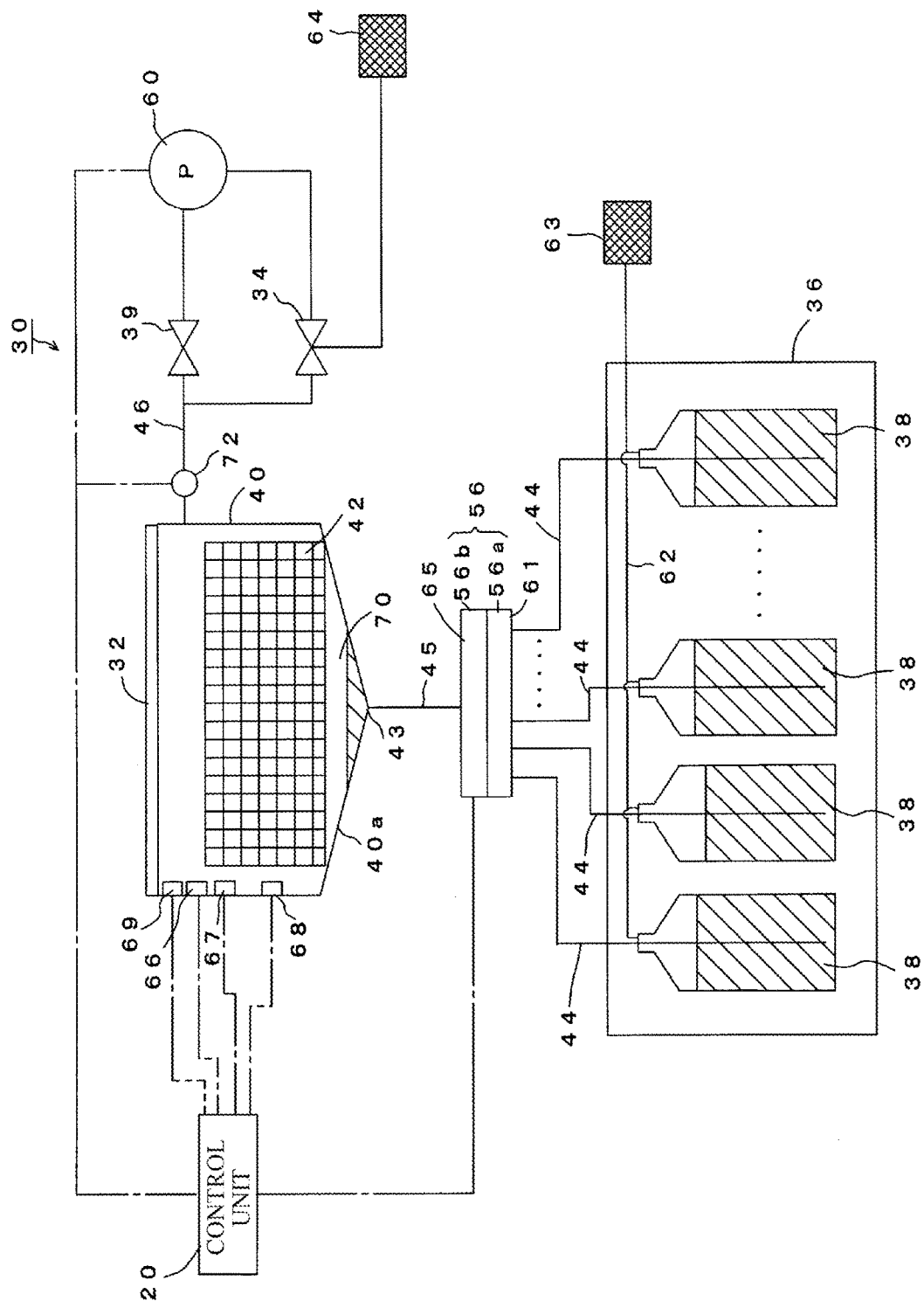
FIG. 5 is an explanatory view illustrating a state in which the liquid chemical is drained to such a degree that air in the treatment tank is not discharged from the state in FIG. 4.

Agitation of the liquid chemical stored in the treatment tank 40 during the tissue piece treatment process will be described on the basis of FIGS. 3 to 5. Here, an example of the immersion treatment using the basket 42 having an ordinary size will be described.

A feature of the present invention is agitation of the liquid chemical by supplying/draining the liquid from the treatment tank 40 so that the tissue piece is exposed from the liquid chemical during treatment of the liquid chemical.

Into the treatment tank 40 in which the basket 42 is disposed, each of the liquid chemicals is supplied in the order illustrated in FIG. 1.

At start of the immersion treatment in each liquid chemical, the control unit 20 controls the pump 60 and the selection valve 56 so that the liquid supply is performed until the liquid chemical exceeds the third liquid level sensor 67 and moreover, it is detected by the first liquid level sensor 66. That is, with respect to the ordinary basket 42, the third liquid level sensor 67 functions as the liquid level guarantee sensor, and the first liquid level sensor 66 functions as the liquid supply stop sensor.

When the first liquid level sensor 66 detects the liquid chemical, the control unit 20 stops the liquid supply. At this time, the basket 42 is in a state fully immersed in the liquid chemical.

After predetermined time has elapsed since the liquid chemical was supplied, the control unit 20 operates the pump 60 and the selection valve 56 and drains the liquid chemical in the treatment tank 40.

The liquid drain is performed until the basket 42 is exposed from the liquid chemical and moreover, the liquid drain is finished before the liquid chemical in the treatment tank 40 is fully drained. As a result, discharge of the air in the treatment tank 40 from the treatment tank 40 is prevented, and the air in the treatment tank 40 can be prevented from being introduced into the liquid chemical tank 38.

In order to stop the liquid drain of the liquid chemical before the liquid chemical is fully drained, the control unit 20 stops the liquid drain when predetermined time has elapsed since the second liquid level sensor 68 detected the liquid level of the liquid chemical. The predetermined time from detection of the liquid level of the liquid chemical by the second liquid level sensor 68 to the liquid drain stop is preferably counted in advance. That is, time from the detection by the second liquid level sensor 68 to the liquid drain when the tissue piece is actually fully exposed and the liquid drain is performed to such a degree that the air in the treatment tank is not discharged from the treatment tank is counted and stored in the control unit 20 in advance.

Moreover, the bottom surface 40a of the treatment tank 40 is provided with inclination at the center, and a gap 70 is formed between the bottom surface of the basket 42 and the supply/drain port 43 of the treatment tank 40. In the liquid drain, the liquid drain is stopped when the liquid chemical is not fully drained and the liquid level is located below the bottom surface of the basket 42.

After the liquid drain is completed, the control unit 20 supplies the same liquid chemical into the treatment tank 40 again. When the first liquid level sensor 66 detects the liquid chemical, the control unit 20 stops the liquid supply. Then, after the predetermined time has elapsed since the liquid chemical was supplied, the control unit 20 operates the pump 60 and the selection valve 56 and drains the liquid chemical in the treatment tank 40.

The liquid drain is performed until the basket 42 is exposed from the liquid chemical similarly to the above, and the liquid drain is finished before the liquid chemical in the treatment tank 40 is fully drained. As a result, discharge of the air in the treatment tank 40 and introduction into the liquid chemical tank 38 can be prevented.

As described above, by repeating the liquid drain and the liquid supply so that the basket is exposed during the immersion treatment in the liquid chemical, the liquid chemical close to the tissue piece can be reliably moved, whereby the immersion treatment in each of the liquid chemicals can be favorably performed.

The control unit 20 repeatedly performs the liquid supply/drain cycle of the liquid supply and the liquid drain in the immersion treatment in one of the liquid chemicals for a number of times set in advance (stored in the control unit 20 in advance).

By means of this repetition of the liquid supply/drain, the liquid chemical close to the tissue piece can be actively moved, and treatment of the tissue piece by each liquid chemical can be performed favorably. Moreover, since the treatment of the tissue piece can be performed favorably by agitation, the time interval at which the liquid supply/drain cycle is performed can be made longer than the prior-art agitation.

Thus, the driving time of the pump and the like can be reduced.

Second Embodiment on Agitation of Liquid Chemical

Figure 6:
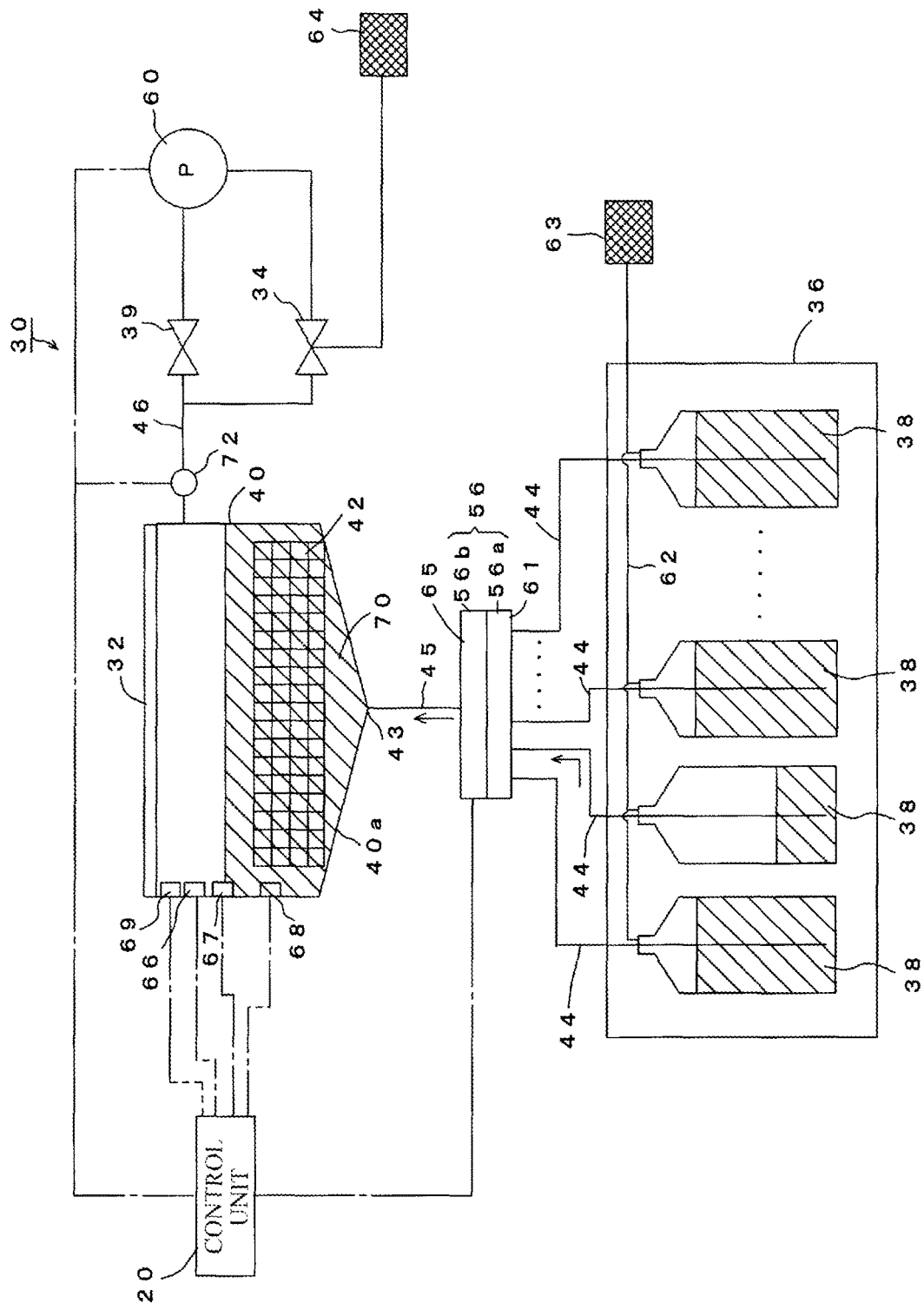
FIG. 6 is an explanatory view illustrating a state in which the liquid chemical is supplied into the treatment tank accommodating a thin basket.
Figure 7:
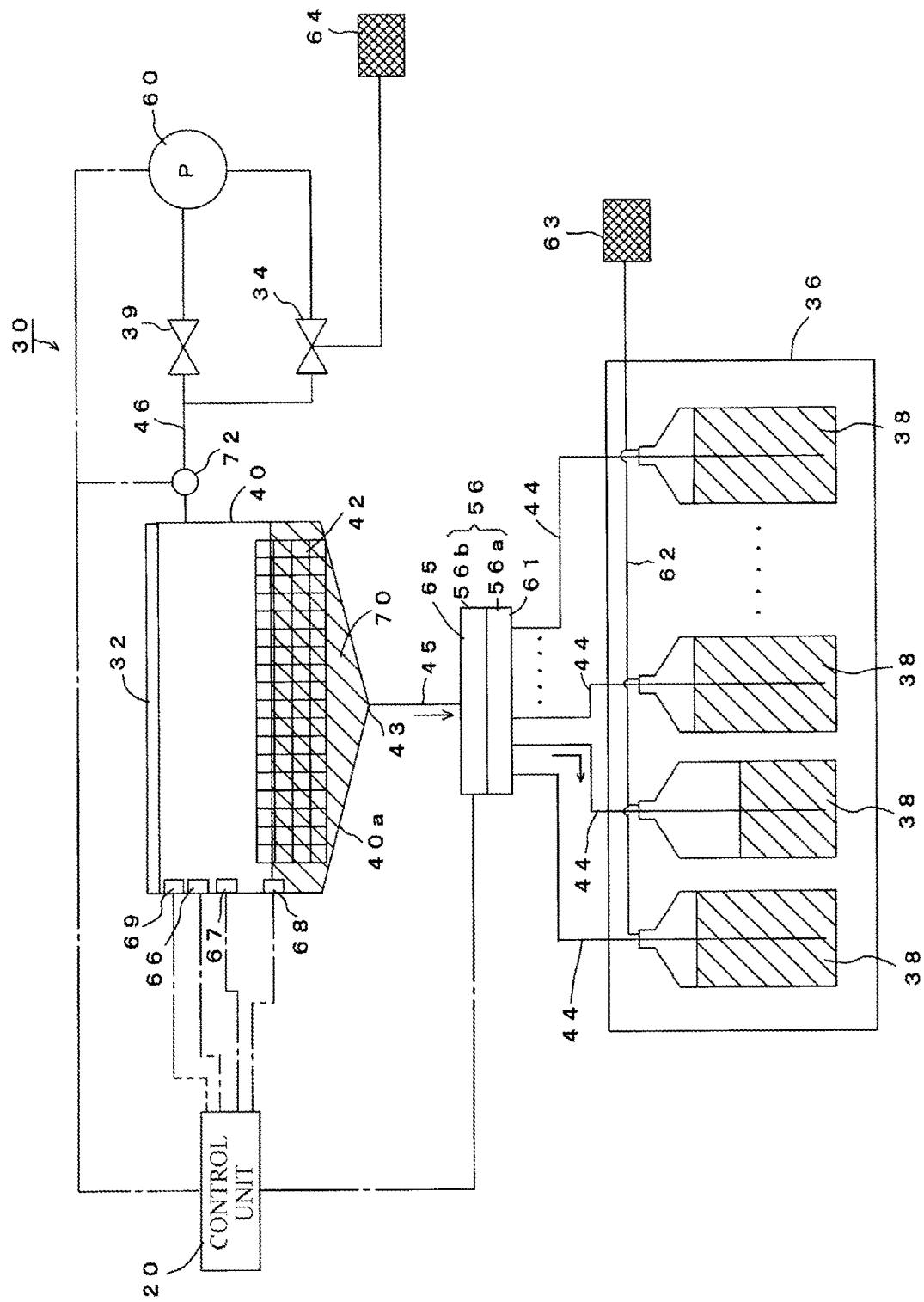
FIG. 7 is an explanatory view illustrating a state in which the liquid chemical is drained to the bottom surface of the basket from the state in FIG. 6.
Figure 8:
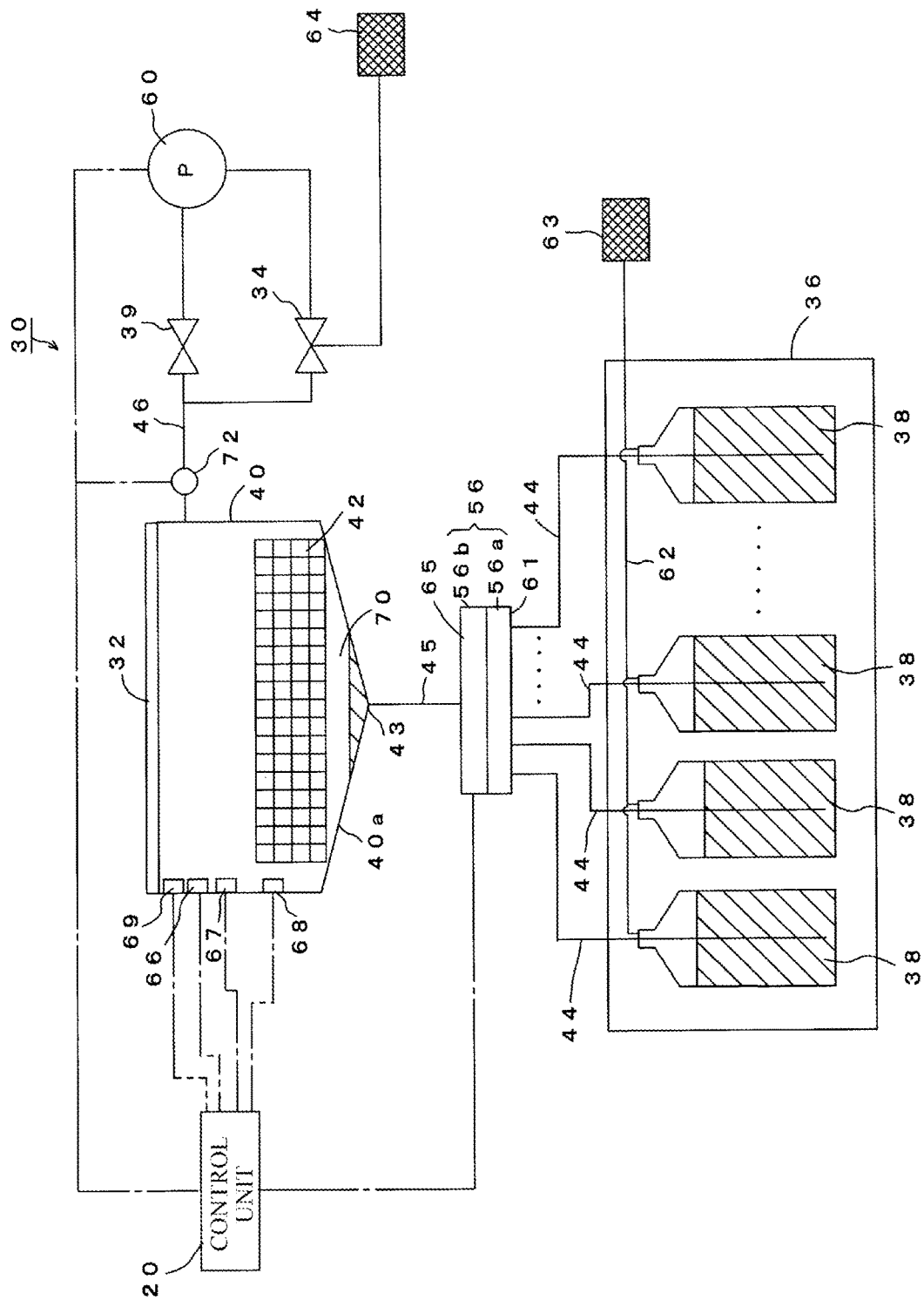
FIG. 8 is an explanatory view illustrating a state in which the liquid chemical is drained to such a degree that the air in the treatment tank is not discharged from the state in FIG. 7.

An example of the immersion treatment using the thin basket 49 will be described on the basis of FIGS. 6 to 8. Here, the thin basket 49 has a height approximately half of that of the aforementioned ordinary basket 42. As illustrated in FIGS. 6 to 8, when only one thin basket 49 is accommodated in the treatment tank 40, the thin basket 49 is accommodated with the height approximately half of the height of the entire treatment tank 40.

Into the treatment tank 40 in which the thin basket 49 is disposed, each of the liquid chemicals is supplied in the order illustrated in FIG. 1.

At start of the immersion treatment in each liquid chemical, the control unit 20 controls the pump 60 and the selection valve 56 so that the liquid supply is performed until the liquid chemical exceeds the second liquid level sensor 68 and moreover, it is detected by the second liquid level sensor 67. That is, with respect to the thin basket 49, the second liquid level sensor 68 functions as the liquid level guarantee sensor, and the third liquid level sensor 67 functions as the liquid supply stop sensor.

When the third liquid level sensor 67 detects the liquid chemical, the control unit 20 stops the liquid supply. At this time, the thin basket 49 is in a state fully immersed in the liquid chemical. The control unit 20 drains the liquid chemical in the treatment tank 40 by operating the pump 60 and the selection valve 56 after the predetermined time has elapsed since the liquid chemical was supplied.

The liquid drain is performed until the thin basket 49 is exposed from the liquid chemical and moreover, the liquid rain is finished before the liquid chemical in the treatment tank 40 is fully drained. As a result, discharge of the air in the treatment tank 40 from the treatment tank 40 is prevented, and the air in the treatment tank 40 can be prevented from being introduced into the liquid chemical tank 38.

In order to stop the liquid drain of the liquid chemical before the liquid chemical is fully drained, the control unit 20 stops the liquid drain when the predetermined time has elapsed since the second liquid level sensor 68 detected the liquid level of the liquid chemical. The predetermined time from detection of the liquid level of the liquid chemical by the second liquid level sensor 68 to the liquid drain stop is preferably counted in advance. That is, time from the detection by the second liquid level sensor 68 to the liquid drain when the tissue piece is actually fully exposed and the liquid drain is performed to such a degree that the air in the treatment tank is not discharged from the treatment tank is counted and stored in the control unit 20 in advance.

In both the cases of the ordinary basket 42 and of the thin basket 49, in an agitation process by the liquid supply/drain cycle, the sensor to be a reference when the liquid chemical is drained is the lowermost second liquid level sensor 68 for both the cases.

In the case of the ordinary basket 42, for example, the third liquid level sensor 67 may be used as a sensor to be the reference when the liquid chemical is drained without using the second liquid level sensor 68. However, when predetermined time from the third liquid level sensor 67 to the completion of the liquid drain is counted, the predetermined time becomes longer than a case in which counting is started from the second liquid level sensor 68, and there is a concern of an error. Thus, the sensor to be the reference when the liquid chemical is drained is preferably the lowermost second liquid level sensor 68.

The control unit 20 needs to execute control such that time required from detection by the second liquid level sensor 68 of the liquid level of the liquid chemical to full drain of the liquid chemical is stored in advance and the liquid drain processing is finished before the stored time has elapsed since the second liquid level sensor 68 detected the liquid level.

Moreover, the bottom surface 40a of the treatment tank 40 is provided with inclination at the center, and the gap 70 is formed between the bottom surface of the basket 42 and the supply/drain port 43 of the treatment tank 40. In the liquid drain, the liquid drain is stopped when the liquid chemical is not fully drained and the liquid level is located below the bottom surface of the basket 42.

After the liquid drain is completed, the control unit 20 supplies the same liquid chemical into the treatment tank 40 again. When the third liquid level sensor 67 detects the liquid chemical, the control unit 20 stops the liquid supply. Then, after the predetermined time has elapsed since the liquid chemical was supplied, the control unit 20 operates the pump 60 and the selection valve 56 and drains the liquid chemical in the treatment tank 40.

The liquid drain is performed until the basket 42 is exposed from the liquid chemical similarly to the above, and the liquid drain is finished before the liquid chemical in the treatment tank 40 is fully drained. As a result, discharge of the air in the treatment tank 40 and introduction into the liquid chemical tank 38 can be prevented.

As described above, by repeating the liquid drain and the liquid supply so that the basket is exposed during the immersion treatment in the liquid chemical, the liquid chemical close to the tissue piece can be reliably moved, whereby the immersion treatment in each of the liquid chemicals can be favorably performed.

The control unit 20 repeatedly performs the liquid supply/drain cycle of the liquid supply and the liquid drain in the immersion treatment in one of the liquid chemicals for a number of times set in advance.

By means of this repetition of the liquid supply/drain, the liquid chemical close to the tissue piece can be actively moved, and treatment of the tissue piece by each liquid chemical can be performed favorably. Moreover, since the treatment of the tissue piece can be performed favorably by agitation, the time interval at which the liquid supply/drain cycle is performed can be made longer than the prior-art agitation.

Thus, the driving time of the pump and the like can be reduced.

Third Embodiment on Agitation of Liquid Chemical

Figure 9:
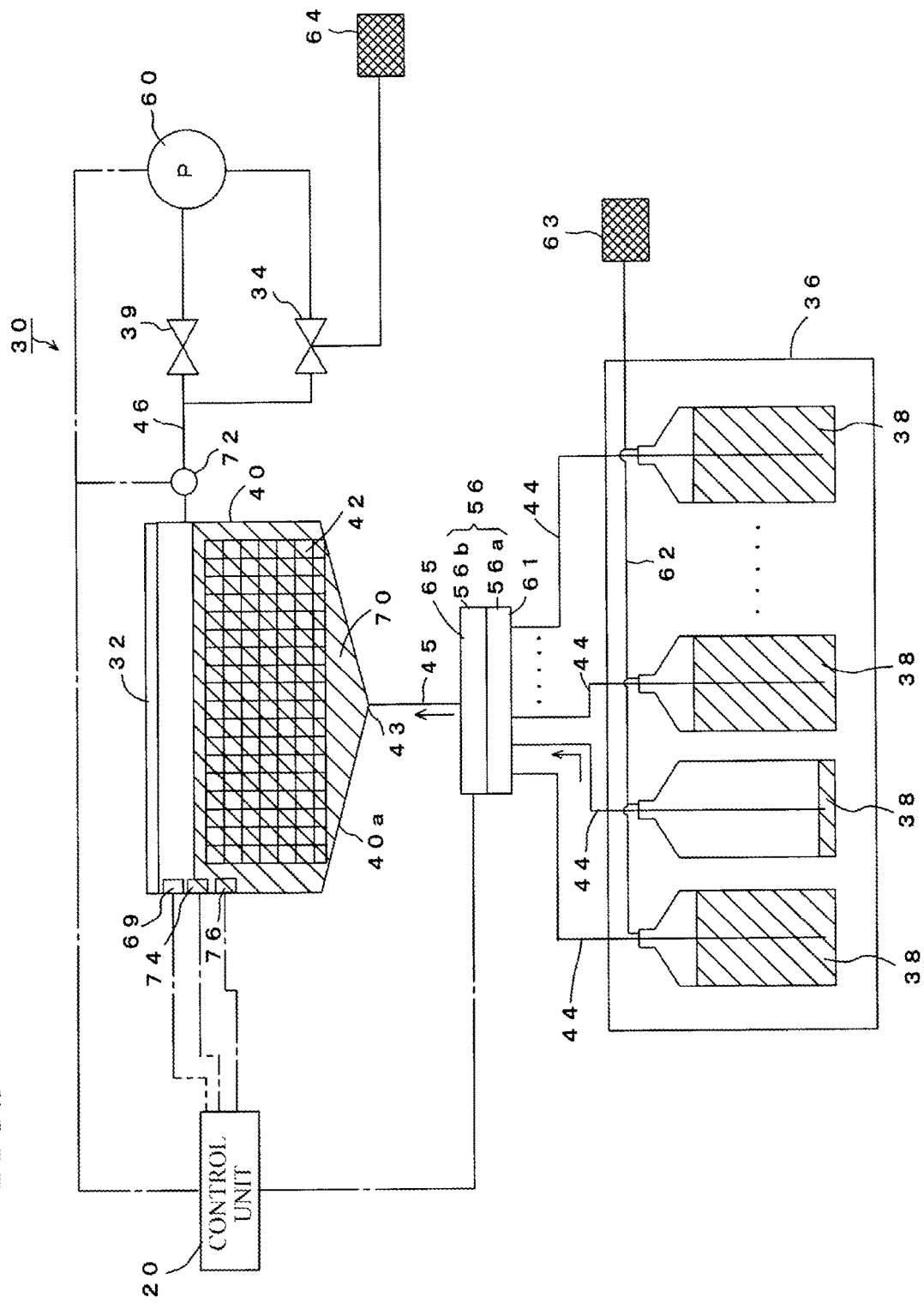
FIG. 9 is an explanatory view illustrating a state in which the liquid chemical is supplied into the treatment tank in another embodiment.
Figure 10:
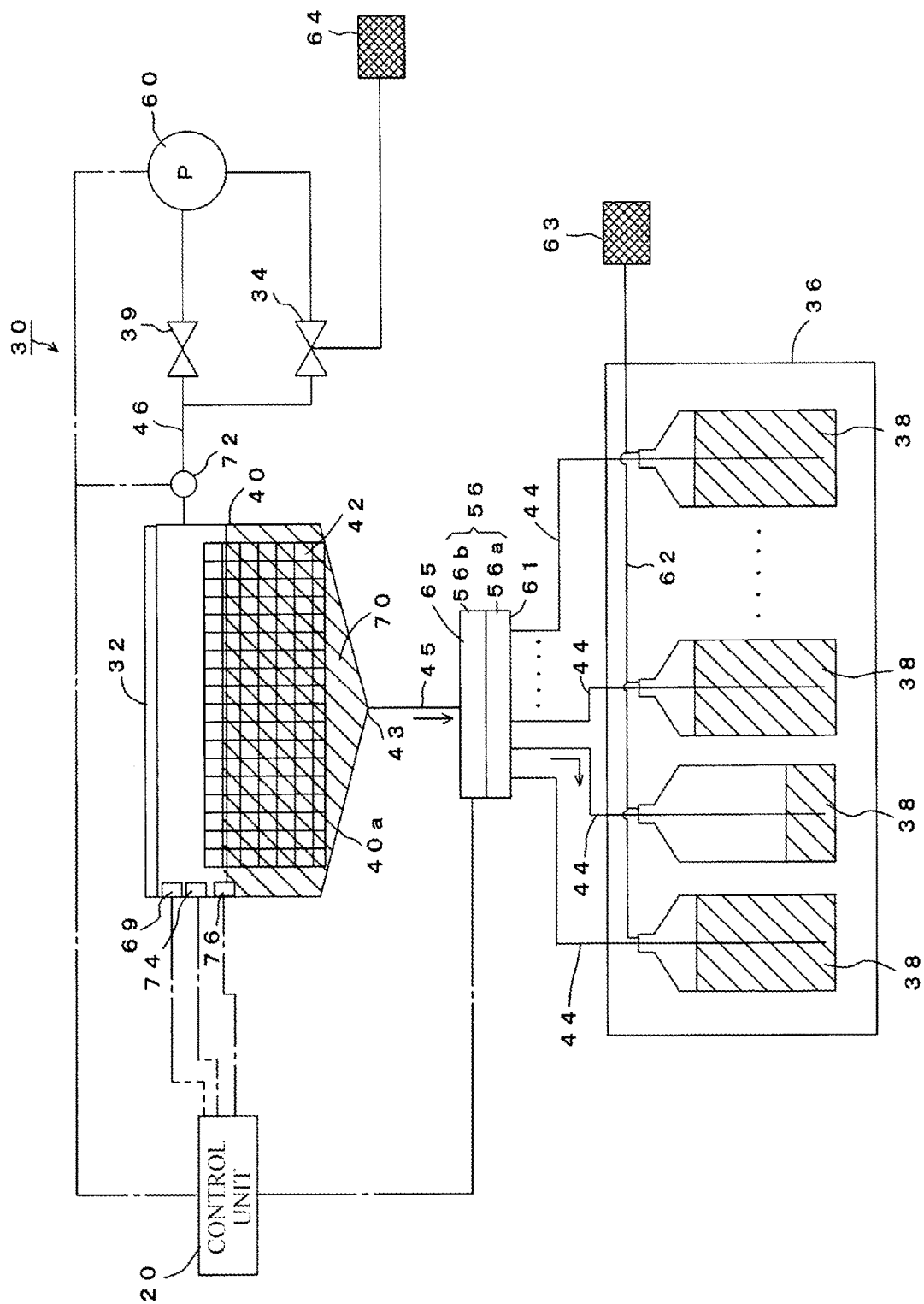
FIG. 10 is an explanatory view illustrating a state in which the liquid chemical is drained to the bottom surface of the basket from the state in FIG. 9.
Figure 11:
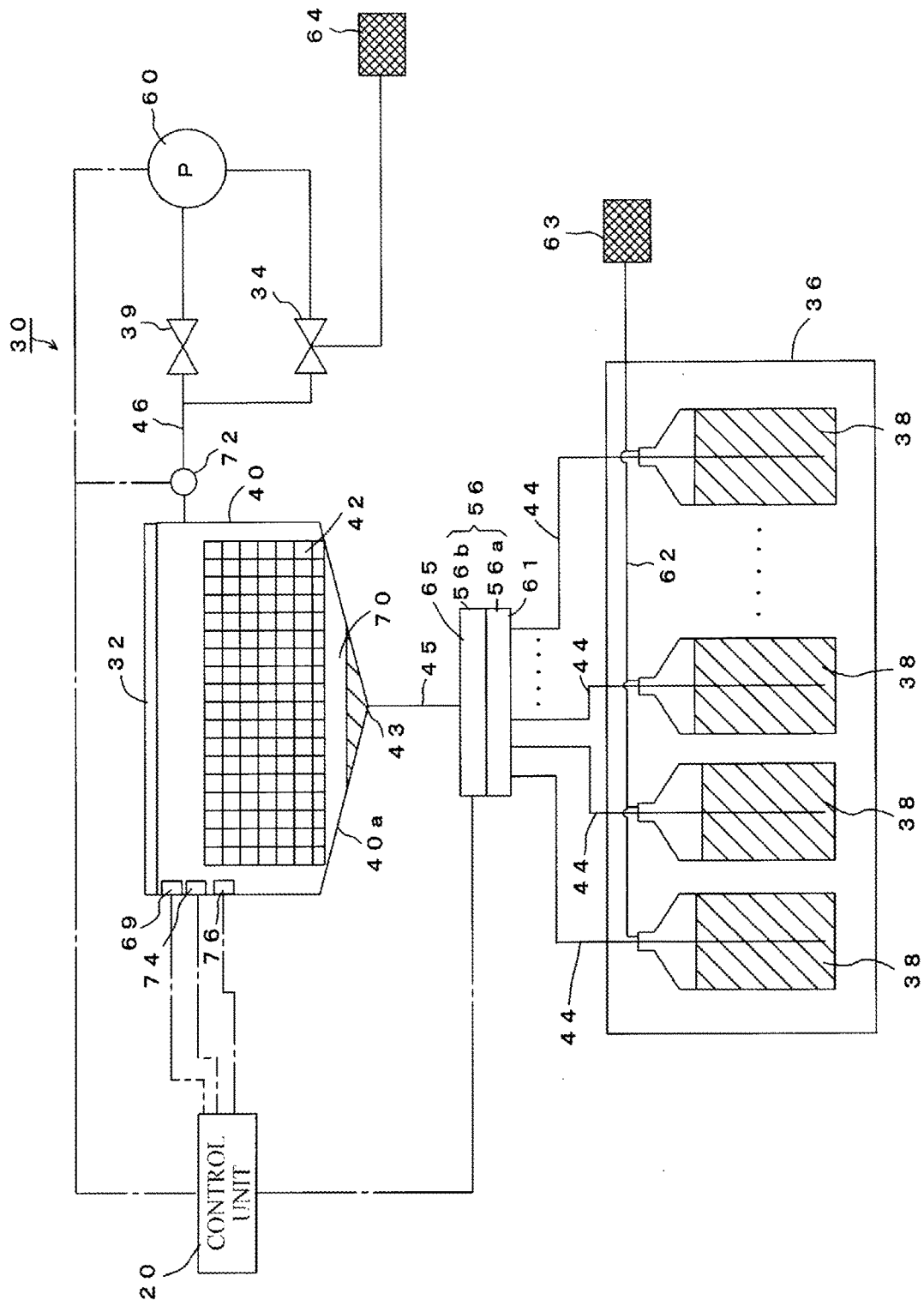
FIG. 11 is an explanatory view illustrating a state in which the liquid chemical is drained to such a degree that the air in the treatment tank is not discharged from the state in FIG. 10.

The immersion treatment in the treatment tank capable of accommodating not a plurality of baskets but only one basket will be described on the basis of FIGS. 9 to 11. In this embodiment, it is assumed that only the ordinary basket 42 in the first embodiment can be accommodated.

On the side wall surface inside the treatment tank 40 in this embodiment, a plurality of the sensors capable of detecting the liquid level is provided, but unlike the aforementioned embodiments, three sensors are disposed in the vertical direction. In the three sensors, the uppermost sensor is the overflow sensor 69. The overflow sensor 69 is provided close to the upper limit of the treatment tank 40 similarly to the aforementioned embodiments and detects the liquid level so that the liquid chemical does not overflow from the treatment tank 40.

Below the overflow sensor 69, two sensors are provided.

In the two sensors, an upper sensor is a liquid supply stop sensor 74 and is provided above the upper surface of the ordinary basket 42 at a liquid supply stop position which is a position where the liquid supply is stopped in the liquid supply of the liquid chemical.

In the two sensors, the lower sensor is a liquid level guarantee sensor 76 and is provided at a liquid level guarantee position guaranteeing that the tissue piece in the ordinary basket 42 is at a position reliably immersed in the liquid chemical.

Each of the aforementioned three sensors is connected to the control unit 20, respectively, and can cause the control unit 20 to recognize that the liquid level is detected at liquid level detection.

Subsequently, the immersion treatment in this embodiment will be described.

Into the treatment tank 40 in which the ordinary basket 42 is disposed, each of the liquid chemicals is supplied in the order illustrated in FIG. 1.

At start of the immersion treatment in each liquid chemical, the control unit 20 controls the pump 60 and the selection valve 56 so that the liquid supply is performed until the liquid chemical exceeds the liquid level guarantee sensor 76 and moreover, it is detected by the liquid supply stop sensor 74.

When the liquid supply stop sensor 74 detects the liquid chemical, the control unit 20 stops the liquid supply. At this time, the ordinary basket 42 is in the state fully immersed in the liquid chemical.

After the predetermined time has elapsed since the liquid chemical was supplied, the control unit 20 operates the pump 60 and the selection valve 56 and drains the liquid chemical in the treatment tank 40.

The liquid drain is performed until the ordinary basket 42 is exposed from the liquid chemical, and the liquid drain is finished before the liquid chemical in the treatment tank 40 is fully drained. As a result, discharge of the air in the treatment tank 40 from the treatment tank 40 can be prevented, and the air in the treatment tank 40 can be prevented from being introduced into the liquid chemical tank 38.

In order to stop the liquid drain of the liquid chemical before the liquid chemical is fully drained, the control unit 20 stops the liquid drain when the predetermined time has elapsed since the liquid level guarantee sensor 76 detected the liquid level of the liquid chemical. The predetermined time from detection of the liquid level of the liquid chemical by the liquid level guarantee sensor 76 to the liquid drain stop is preferably counted in advance. That is, time from the detection by the liquid level guarantee sensor 76 to the liquid drain when the tissue piece is actually fully exposed and the liquid drain is performed to such a degree that the air in the treatment tank is not discharged from the treatment tank is counted and stored in the control unit 20 in advance.

Moreover, the bottom surface 40a of the treatment tank 40 is provided with inclination at the center, and the gap 70 is formed between the bottom surface of the basket 42 and the supply/drain port 43 of the treatment tank 40. In the liquid drain, the liquid drain is stopped when the liquid chemical is not fully drained and the liquid level is located below the bottom surface of the basket 42.

After the liquid drain is completed, the control unit 20 supplies the same liquid chemical into the treatment tank 40 again. When the liquid level detection sensor 76 detects the liquid chemical and then, the liquid supply stop sensor 74 detects the liquid chemical, the control unit 20 stops the liquid supply. Then, after the predetermined time has elapsed since the liquid chemical was supplied, the control unit 20 operates the pump 60 and the selection valve 56 and drains the liquid chemical in the treatment tank 40.

The liquid drain is performed until the basket 42 is exposed from the liquid chemical similarly to the above, and the liquid drain is finished before the liquid chemical in the treatment tank 40 is fully drained. As a result, discharge of the air in the treatment tank 40 and introduction into the liquid chemical tank 38 can be prevented.

As described above, by repeating the liquid drain and the liquid supply so that the basket is exposed during the immersion treatment in the liquid chemical, the liquid chemical close to the tissue piece can be reliably moved, whereby the immersion treatment in each of the liquid chemicals can be favorably performed.

The control unit 20 repeatedly performs the liquid supply/drain cycle of the liquid supply and the liquid drain in the immersion treatment in one of the liquid chemicals for a number of times set in advance (stored in the control unit 20 in advance).

By means of this repetition of the liquid supply/drain, the liquid chemical close to the tissue piece can be actively moved, and treatment of the tissue piece by each liquid chemical can be performed favorably. Moreover, since the treatment of the tissue piece can be performed favorably by agitation, the time interval at which the liquid supply/drain cycle is performed can be made longer than the prior-art agitation.

Thus, the driving time of the pump and the like can be reduced.

In this embodiment, the liquid supply/drain cycle is performed by the sensor provided at the liquid level guarantee position in the ordinary basket 42 and the sensor provided at the liquid supply stop position, and the liquid chemical is agitated.

However, even in the case in which a plurality of the thin baskets 49 as described in the second embodiment is stacked vertically to the height equal to or substantially equal to the single ordinary basket 42, the liquid supply/drain cycle is performed by the sensor provided at the liquid level guarantee position in the ordinary basket 42 and the sensor provided at the liquid supply stop position, and the liquid chemical can be agitated.

Fourth Embodiment on Agitation of Liquid Chemical

In each of the aforementioned embodiments, a measure which should be taken when the air in the treatment tank is discharged in the liquid drain will be described.

Whether or not the air in the treatment tank has been discharged is determined by the pressure sensor 72 for detecting the pressure in the treatment tank and the control unit 20 connected to the pressure sensor 72.

When the liquid chemical in the amount that the entire basket is exposed in the treatment tank is drained from the treatment tank for agitation of the liquid chemical during the execution of the immersion treatment by the liquid chemical, if the pressure sensor 72 detects a pressure drop in the treatment tank, the control unit 20 modifies the predetermined time set in advance from detection of the liquid level by the second liquid level sensor 68 or the predetermined time from the detection of the liquid level by the liquid level guarantee sensor 76.

The control unit 20 stores predetermined time set again by reducing time from the predetermined time set in advance.

Then, when the liquid chemical in the amount that the entire basket is exposed in the treatment tank is drained from the treatment tank for agitation of the liquid chemical next time, the liquid drain is stopped on the basis of time obtained by setting the predetermined time from the detection of the liquid level by the second liquid level sensor 68 or the predetermined time from the detection of the liquid level by the liquid level guarantee sensor 76 again.

Thus, even if the air in the treatment tank is discharged, the air in the treatment tank can be prevented from being discharged in the liquid drain processing next time.

The number of the sensors and arrangement position of the sensor are not limited to each of the aforementioned embodiments.

What is claimed is:

1. A tissue piece treating method in which different liquid chemicals are supplied to a treatment tank where a basket accommodating a tissue piece is disposed inside, the liquid chemicals are supplied in a predetermined order and each of the liquid chemicals is agitated without an agitating device while performing immersing steps in each of the liquid chemicals, comprising the steps of:

supplying a first of the different liquid chemicals to the treatment tank until the basket is in a state fully immersed in the first of the different liquid chemicals;

after a predetermined time elapse since the first of the different liquid chemicals is supplied, draining the first of the different liquid chemicals from the treatment tank until the entire basket is exposed from the first of the different liquid chemicals;

after the first of the different liquid chemicals is drained from the treatment tank, resupplying the same first of the different liquid chemicals to the treatment tank until the basket is in the state fully immersed in the first of the different liquid chemicals;

after a predetermined time elapse since the first of the different liquid chemicals is resupplied to the treatment tank, draining the first of the different liquid chemicals from the treatment tank until the entire basket is exposed from the first of the different liquid chemicals;

repeating the supply and the drain of the first of the different liquid chemicals at least once so as to agitate the first of the different liquid chemicals in the treatment tank and individually supplying the one or more other of the different liquid chemicals according to the same steps as the first of the different liquid chemicals, wherein the repeated supplying and draining of each of the different liquid chemicals washes the surface of the tissue piece and performs dehydration/degreasing.

2. The tissue piece treating method according to claim 1, wherein when the liquid amount in such an amount that the entire basket is exposed in the treatment tank is drained from the treatment tank, the liquid is drained so that air in the treatment tank is not discharged.

3. The tissue piece treating method according to claim 2, wherein in said treatment tank, a liquid level guarantee sensor for detecting one of the different liquid chemicals at a liquid level guarantee position which is a position where the entire tissue piece in the basket is immersed in the one of the different liquid chemicals is provided; and when the one of the different liquid chemicals in the amount that the entire basket is exposed in the treatment tank is to be drained from the treatment tank, by constituting such that the liquid drain is finished after predetermined time set in advance has elapsed since said liquid level guarantee sensor detected a liquid level of the one of the different liquid chemicals, the entire basket is exposed in the treatment tank and the air in the treatment tank is prevented from being discharged.

4. The tissue piece treating method according to claim 3, wherein in said treatment tank, a liquid supply stop sensor for detecting the one of the different liquid chemicals at a liquid supply stop position which is a position above an upper surface position of the basket and where liquid supply is stopped is provided; and when the liquid is supplied into the treatment tank so that the entire basket is immersed, the liquid supply is stopped when the liquid supply stop sensor detects the liquid level of the one of the different liquid chemicals.

5. The tissue piece treating method according to claim 3, wherein a pressure sensor for detecting a pressure in the treatment tank is provided in the tissue piece treating apparatus;

when the one of the different liquid chemicals in such an amount that the entire basket is exposed in the treatment tank is drained from the treatment tank, if the pressure sensor detects a pressure drop in the treatment tank, said predetermined time set in advance is reduced and set again; and when the one of the different liquid chemicals in the amount that the entire basket is exposed in the treatment tank is drained from the treatment tank, said liquid level guarantee sensor detects the liquid level of the one of the different liquid chemicals and the liquid drain is finished after the predetermined time set again has elapsed, whereby the entire basket is exposed in the treatment tank and the air in the treatment tank is not discharged.

6. The tissue piece treating method according to claim 4, wherein sensors each capable of detecting a liquid level are provided at a plurality of positions corresponding to a height of each of the baskets in the treatment tank so that said liquid supply/drain cycle can be repeatedly performed in accordance with a height of each basket even if the baskets with different heights are accommodated or a plurality of the baskets is stacked and accommodated;

when the liquid supply/drain cycle is to be performed to the basket with a low height, the sensor provided at a lowermost position is used as the liquid level guarantee sensor, and the liquid supply/drain cycle is performed by using the sensor disposed above the upper surface position of the basket with the low height as a liquid supply stop sensor; and when the liquid supply/drain cycle is to be performed to the basket with a high height or to the baskets each with the low height stacked in plural stages, not the liquid level guarantee sensor corresponding to the basket with the high height or the basket with the low height, but the sensor provided at the lowermost position detects the liquid level of the one of the different liquid chemicals and then, the liquid drain is finished after the predetermined time set in advance has elapsed, and the liquid supply/drain cycle is performed by using the sensor disposed above the upper surface position of the basket with the high height or the baskets each with the low height stacked in plural as the liquid supply stop sensor.

7. The tissue piece treating method according to claim 4, wherein a pressure sensor for detecting a pressure in the treatment tank is provided in the tissue piece treating apparatus;

when the one of the different liquid chemicals in such an amount that the entire basket is exposed in the treatment tank is drained from the treatment tank, if the pressure sensor detects a pressure drop in the treatment tank, said predetermined time set in advance is reduced and set again; and when the one of the different liquid chemicals in the amount that the entire basket is exposed in the treatment tank is drained from the treatment tank, said liquid level guarantee sensor detects the liquid level of the one of the different liquid chemicals and the liquid drain is finished after the predetermined time set again has elapsed, whereby the entire basket is exposed in the treatment tank and the air in the treatment tank is not discharged.

* * * * *